US012669433B2

(12) United States Patent (10) Patent No.: US 12,669,433 B2
Decaux et al. (45) Date of Patent: Jun. 30, 2026

(54) METHOD FOR ANALYZING A BIOLOGICAL SAMPLE COMPRISING DETERMINATION OF THE SPATIAL DISTRIBUTION OF BIOMASS ALONG THE OPTICAL AXIS

(71) Applicant: BIOMERIEUX, Marcy L'Etoile (FR)

(72) Inventors: Dominique Decaux, Chaponost (FR);
Emilie Bisceglia, La Tour de Salvagny (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 621 days.

(21) Appl. No.: 18/025,814

(22) PCT Filed: Sep. 23, 2021

(86) PCT No.: PCT/FR2021/051635
§ 371 (c)(1),
(2) Date: Mar. 10, 2023

(87) PCT Pub. No.: WO2022/064147
PCT Pub. Date: Mar. 31, 2022

(65) Prior Publication Data
US 2024/0019365 A1 Jan. 18, 2024

(30) Foreign Application Priority Data

Sep. 25, 2020 (FR) ...................................... 2009779

(51) Int. Cl.
G01N 21/45 (2006.01)
C12M 1/34 (2006.01)
C12Q 1/02 (2006.01)
(52) U.S. Cl.
CPC ........... G01N 21/453 (2013.01); C12M 41/36 (2013.01); C12Q 1/02 (2013.01)

(58) Field of Classification Search
CPC ......... C12M 41/36; C12Q 1/02; G01N 15/14; G01N 15/1434; G01N 2015/1006;
(Continued)

(56) References Cited

U.S. PATENT DOCUMENTS

2020/0096941 A1 3/2020 Tatsuta et al.

FOREIGN PATENT DOCUMENTS

EP 3 252 455 A1 12/2017
WO 2016/062296 A1 4/2016

OTHER PUBLICATIONS

Park et al., "Quantitative phase imaging in biomedicine," Nature Photonics, Oct. 2018, vol. 12, pp. 578-589.
(Continued)

*Primary Examiner* — Lydia Edwards
(74) *Attorney, Agent, or Firm* — Oliff PLC

(57) ABSTRACT
A method of analyzing a biological sample including biological agents and disposed in an analysis receptacle in a field of view of a holographic imaging system defining an acquisition focal plane, including, for each of a plurality of measurement times: acquiring a plurality of holographic images of the biological sample at different respective positions of the acquisition focal plane, and, from each acquired holographic image, determining a value of a biomass parameter representative of the quantity of biological agents at the position of the acquisition focal plane, the method including constructing a distribution indicator from values of the biomass parameter at the same measurement time for a plurality of positions of the acquisition focal plane, and providing, among the analysis results, a representation of the distribution of the biomass of biological agents, derived from at least one distribution indicator at a measurement time.

12 Claims, 3 Drawing Sheets

(58) Field of Classification Search
CPC ... G01N 2015/1454; G01N 2015/1486; G01N
21/453; G01N 15/1433; H04N 19/503;
H04N 19/105; H04N 19/52
See application file for complete search history.

(56) References Cited

OTHER PUBLICATIONS

Langehanenberg et al., "Automated three-dimensional tracking of living cells by digital holographic microscopy," Journal of Biomedical Optics, Jan./Feb. 2009, vol. 14, No. 1, pp. 014018-1-014018-7.
Jan. 26, 2022 International Search Report issued in International Patent Application No. PCT/FR2021/051635.

FIG 3

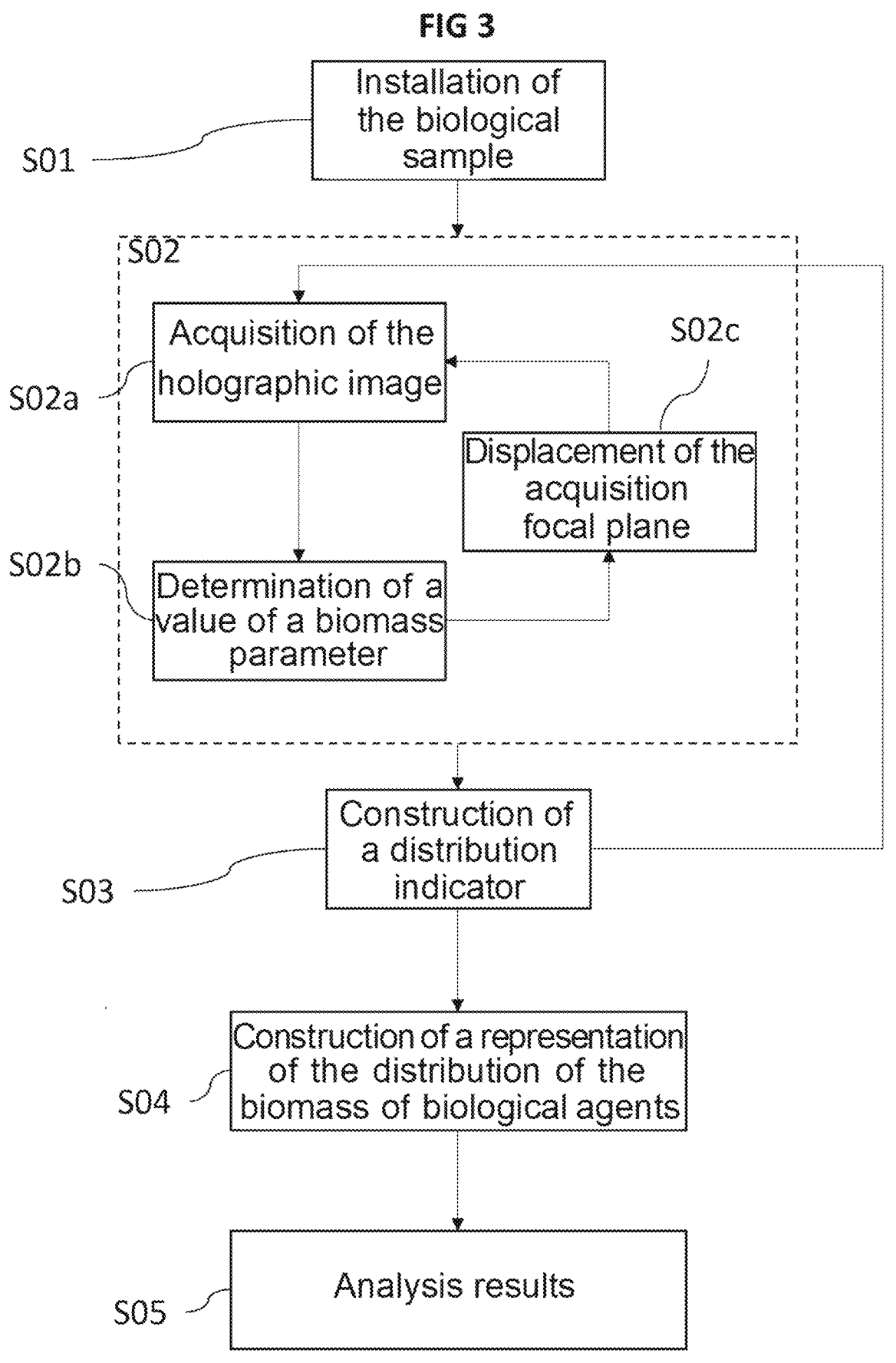

S01 — Installation of the biological sample

S02

S02a — Acquisition of the holographic image

S02c — Displacement of the acquisition focal plane

S02b — Determination of a value of a biomass parameter

S03 — Construction of a distribution indicator

S04 — Construction of a representation of the distribution of the biomass of biological agents S05 — Analysis results

METHOD FOR ANALYZING A BIOLOGICAL SAMPLE COMPRISING DETERMINATION OF THE SPATIAL DISTRIBUTION OF BIOMASS ALONG THE OPTICAL AXIS

TECHNICAL FIELD

The present invention relates to the field of the analysis of biological samples by imaging, and more particularly relates to the monitoring over time of the spatial distribution of biomass along the optical axis.

TECHNOLOGICAL BACKGROUND

The analysis of biological samples by imaging makes use of an optical analysis instrument in which the biological samples to be analyzed are introduced. A biological sample is formed by a suspension of biological agents. The biological agents are for example micro-organisms (bacteria, yeasts, molds, etc.). The analysis of a biological sample is an in vitro analysis applied to the biological sample. The analysis of a biological agent in the biological sample may comprise the identification of said biological agent or the determination of a characteristic of this biological agent, such as for example the minimum inhibiting concentration of an antibiotic which would be effective against said biological agent or else the capacity to form a biofilm.

The biological sample, called inoculum in its initial state, is disposed in a receptacle, or well, at least partially transparent through which the analysis instrument can perform measurements of optical properties of the biological sample. The well contains a nutrient medium and also one or more reagents, such as an enzyme substrate or antibiotics, designed to interact with biological agents present in the biological sample. Generally, a plurality of wells are provided for each to receive inoculum, each of the wells containing different reagents or the same reagent at different concentrations. Depending on the nature of the biological agents present in the inoculum, these react with certain reagents and not with other reagents, or at certain concentrations and not at others. For example, in the framework of an antibiogram for testing the sensitivities to antibiotics, the reagents are composed of various antibiotics at various concentrations, and the biological agents will multiply in the well containing the antibiotics to which they are not sensitive or in which the concentration of antibiotics is insufficient, or on the contrary will see their development more or less hindered in the well containing the antibiotics to which they are sensitives at sufficient concentrations.

These differences in interactions between the biological agents and the reagents therefore result in different developments of the biomass in the well. The biomass, in other words the quantity of biological material present within each well, has a direct influence on the optical properties of the biological sample present in each well, since the biological agents themselves exhibit optical properties different from the solution in which they are in suspension.

In particular, the transmittance of the biological sample is affected by the variation in the concentration of biological agents. For this reason, methods for analyzing biological samples had been developed based on the determination of the variation over time, during an incubation phase, of the overall transmittance (or absorbance, which is equivalent) of a well filled with the biological sample, in order to determine a measurement of turbidity, expressed typically in McFarland (McF). This measurement of turbidity is directly representative of the biomass of biological agents in the biological sample. For this purpose, a light-emitting diode illuminates the sample with a light beam of known intensity, and a single photodiode disposed opposite the light-emitting diode with respect to the sample allows the light intensity received after the light beam has passed through the biological sample to be determined. However, such a measurement in transmittance has quite a low sensitivity, such that it is not possible to measure a turbidity of less than 0.05 McF, or even less than 0.1 McF. Moreover, the biomass does not always allow the concentration of biological agents to be determined: in the case of an increase in the volume of the biological agents, for example by elongation for bacteria, the biomass increases for the same number of biological agents.

Furthermore, the measurement is a global measurement, which does not take into account the spatial distribution of the biological agents within the analysis receptacle, and in particular along the optical axis (commonly denoted by the coordinate z). Indeed, this distribution may be highly non-uniform. For example, certain biological agents develop preferentially in certain areas of the receptacle, and the determination of this non-uniformity may then help to identify the biological agents and/or to determine some of their properties during the analysis of the biological sample. In addition, it is common for the reagents to be disposed on a wall of the analysis receptacle. The spatial distribution of the growth of the biomass of biological agents is thus affected, at least in a transient manner, by the spatial non-uniformity of the reagents, but a global measurement does not allow this to be determined. In particular, non-uniformity can indicate that a biological agent is likely to form a biofilm, in which case particular measures may be taken, for example by adapting a medical treatment to the presence of a biofilm.

PRESENTATION OF THE INVENTION

The invention is therefore aimed, during the analysis of a biological sample, at providing for the latter the variation over time of the spatial distribution of biomass of biological agents along an optical axis, for example in order to reveal characteristics of the biological agents such as the capacity to form a biofilm.

For this purpose, the invention provides a method for analyzing a biological sample by means of an analysis instrument, the biological sample comprising biological agents and being disposed in an analysis receptacle within a field of view of a holographic imaging system, said holographic imaging system defining an optical axis and an acquisition focal plane, the method comprising, for each measurement time from a plurality of measurement times of a measurement period:

the acquisition of a plurality of holographic images of the biological sample at various respective positions on the optical axis of the acquisition focal plane, the determination, based on each acquired holographic image, of a value of a biomass parameter representative of the quantity of biological agents at the position of the acquisition focal plane of said holographic image, the method comprising the construction of a distribution indicator using values of the biomass parameter from one measurement time for several positions of the acquisition focal plane, said distribution indicator being representative of the spatial distribution of the quantity of biological agents in the analysis receptacle along the optical axis at said measurement time, and the provision, from amongst the analysis results, of a representation of the distribution of the biomass of biological agents derived from at least one distribution indicator at one measurement time.

The invention is advantageously completed by the following various features taken alone or according to their various possible combinations:

the distribution indicator is obtained by spatially organizing values of the biomass parameters according to the respective positions of the acquisition focal plane or the distribution indicator is obtained by a calculation applied to values of biomass parameters at various positions of the acquisition focal plane;

the representation of the distribution of the biomass of biological agents is a representation of the time variation of the distribution of the biomass of biological agents which is derived from several distribution indicators at a plurality of measurement times;

the method comprises the construction of the representation of the time variation of the distribution of the biomass of biological agents by spatially organizing distribution indicators according to their respective measurement times;

the biomass parameter of a holographic image is derived from a statistic relating to the gray levels of the pixels of said holographic image;

the biomass parameter is an average of the absolute values of the gray levels of each pixel of the holographic image;

the determination of the biomass parameter of a holographic image comprises a prior normalization of the holographic image, comprising:

the determination of a background image by application of a smoothing filter to the acquired holographic image, the division pixel to pixel of the gray levels of the holographic image acquired by the gray levels of the background image;

the various respective positions on the optical axis of the acquisition focal planes are at least 10 in number in the analysis receptacle, and preferably at least 20;

the analysis receptacle comprises two opposing transparent faces situated at various positions on the optical axis, and the various respective positions on the optical axis of the acquisition focal planes extend from one transparent face to the other transparent face;

at least one position of an acquisition focal plane on the optical axis is not situated between the two transparent faces, and/or a position of an acquisition focal plane on the optical axis corresponds to the position of a transparent face;

the holographic imaging system defines a depth of field of at least 100 μm of depth in the direction of the optical axis around each acquisition focal plane;

the holographic image is a hologram or an image reconstructed from a hologram.

The invention also relates to an analysis instrument comprising a holographic system with a field of view configured for acquiring a holographic image and data processing means, the analysis instrument being configured for receiving a biological sample in an analysis receptacle in the field of view of the holographic system and for implementing the steps of the method according to the invention.

PRESENTATION OF THE FIGURES

Other features, aims and advantages of the invention will become apparent from the description that follows, which is purely illustrative and non-limiting, and which must be read with regard to the appended drawings in which:

FIG. 3 is a diagram illustrating steps of the analysis method according to one possible embodiment of the invention;

DETAILED DESCRIPTION

The method for analyzing a biological sample is carried out by means of an analysis instrument comprising a holographic imaging system with a field of view, the analysis instrument being configured for receiving a biological sample in an analysis receptacle in the field of view of the holographic imaging system.

Figures 1, 2:
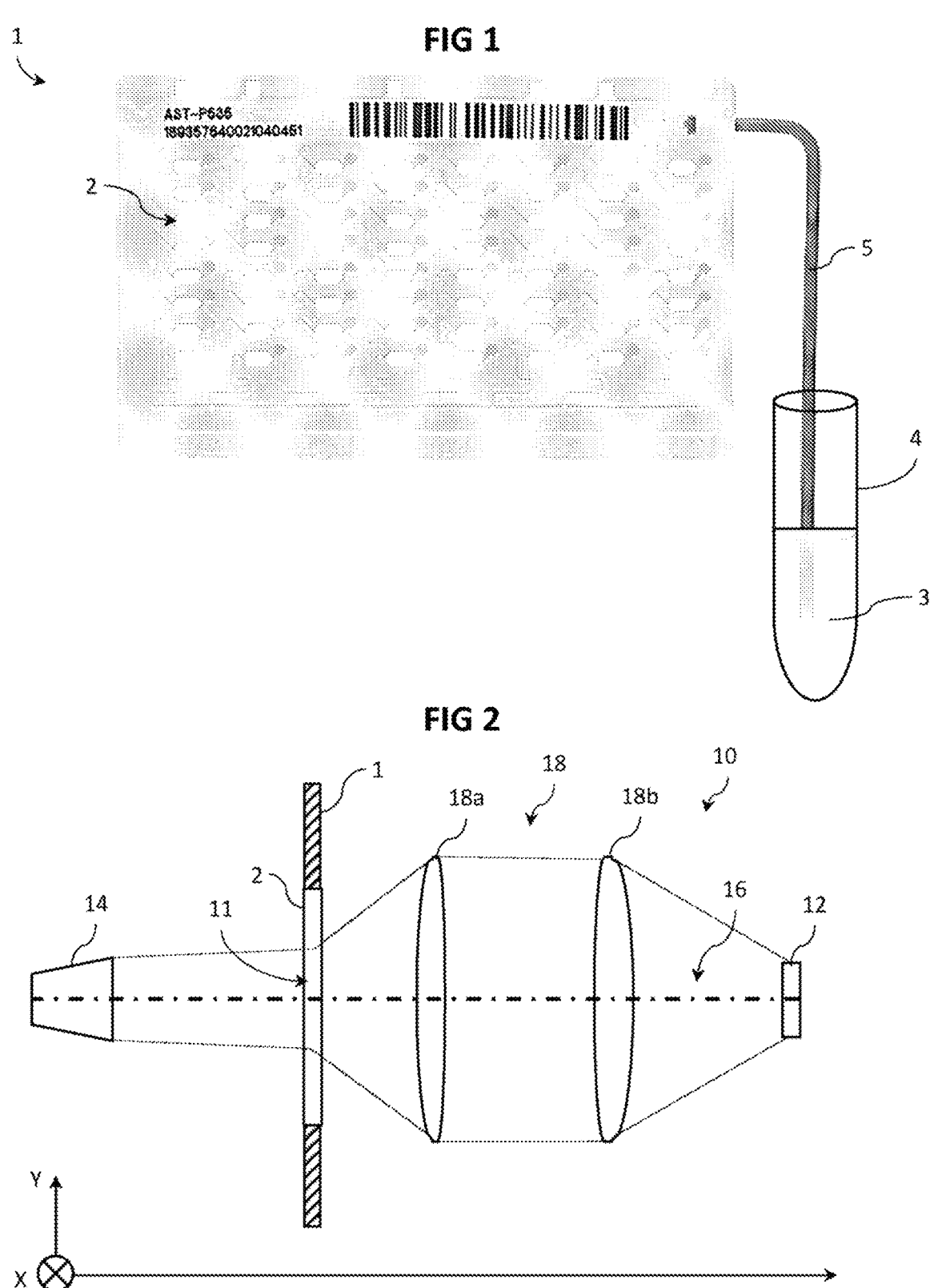
FIG. 1 shows one example of an analysis chart comprising a plurality of receptacles in the form of a well which may be used for the installation of a biological sample to be analyzed, according to one possible embodiment of the invention.
FIG. 2 shows schematically one example of a holographic imaging system which may be used in an analysis instrument according to one possible embodiment of the invention.

FIG. 1 shows one example of analysis chart 1 comprising a plurality of analysis receptacles 2 in the form of a well able to be used for the installation of a biological sample to be analyzed. The analysis receptacles 2 here are organized according to a two-dimensional array on a plane, each receptacle 2 being associated with different analysis conditions, typically by means of different reagents presents in the analysis receptacles 2. For example, in the framework of an antibiogram for testing the sensitivities to antibiotics, the reagents are composed of various antibiotics at various concentrations. The use of an analysis chart 1 is not required, but such an analysis chart 1 allows a plurality of tests to be performed for the same duration of analysis in a standardized manner.

Figure 4:
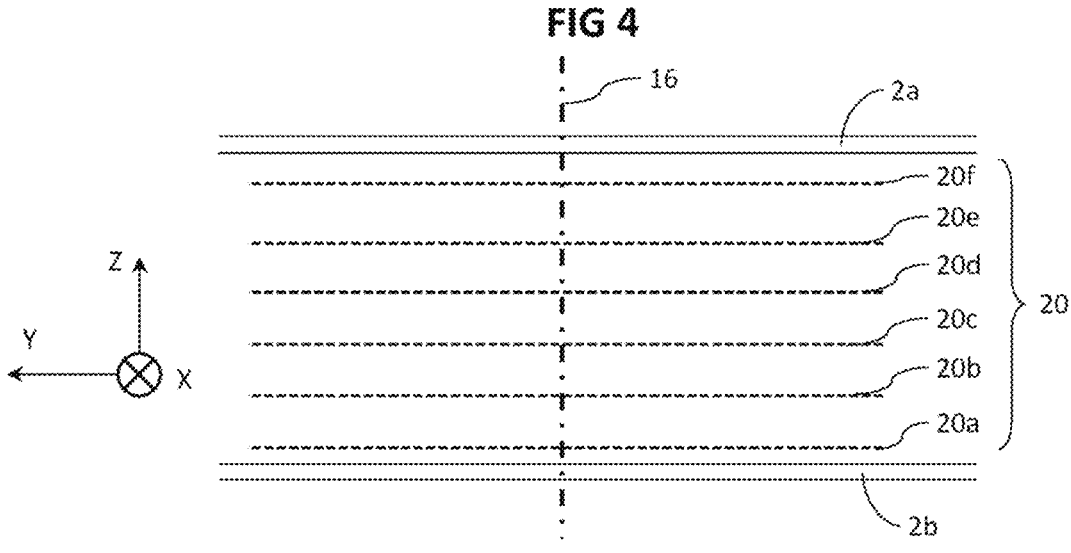
FIG. 4 is a schematic view of a cross-section of an analysis receptacle across a plane containing the optical axis.

Each analysis receptacle 2 is at least partially transparent at at least one wavelength of light, visible or otherwise, and preferably is at least partially transparent for the visible spectrum. This transparency allows the analysis of the biological sample which is contained in it by optical means such as a holographic imaging system. Preferably, and as can be seen in FIG. 4, an analysis receptacle 2 has at least two opposing transparent faces 2a, 2b, so as to present a transparent axis for the propagation of the light. These two opposing transparent faces 2a, 2b are for example separated by less than 10 mm, and preferably less than 5 mm. Typically, the opposing transparent faces 2a, 2b are separated, along the optical axis 16, by more than 0.1 mm, and preferably more than 0.5 mm, and more preferably more than 1 mm. Typically, the opposing transparent faces 2a, 2b are transparent films defining the analysis receptacle 2. It is common for the reagents to be fixed onto at least one of the transparent faces. The reagents may thus be introduced into the analysis receptacle 2 by depositing them onto the film intended to form a transparent face 2a, 2b, before the latter is applied to the analysis chart 1.

In order to allow the filling of the analysis receptacles 2, such an analysis chart 1 may for example comprise a conduit 5 designed to be immersed into a volume 3 of inoculum 3 prepared in a tube 4. The inoculum is prepared by an operator who introduces biological agents, for example sampled from a culture in a Petri dish by means of a swab, into suspension in a saline solution, with a dilution corresponding to a given range of turbidity, for example between 0.5 and 0.63 McF for bacteria as biological agents or else between 1.8 and 2.2 McF for yeasts as biological agents, the range depending on the type of analysis carried out and on the measurement instrument. This initial suspension is subsequently further diluted, for example by a factor 20, or even 100, for analyzing Gram-bacteria or by a factor 10, or even 100, for analyzing Gram+ bacteria. This subsequent dilution may notably be automated, and hence be carried out by the measurement instrument after the installation of the tube 4 into the analysis instrument. It goes without saying that other given ranges of turbidity may be used, depending on the protocols used. The desired dilution may be obtained in one go, or as in the example hereinabove, in several goes.

One end of the conduit 5 is then immersed into the volume 3 of inoculum resulting from the preparation in the tube 4, and the whole thing is introduced into the analysis instrument. All or part of these preparation steps may of course be automated. The inoculum travels through the conduit 5, then via a fluid circulation circuit arranged in the analysis chart 1 and is distributed between the analysis receptacles 5. This movement of the inoculum within the conduit 5 and the analysis chart 1 may be driven by capillarity and/or by a depressurization of the air present at the open end of the tube 4. For example, with the depressurization, the air present in the analysis chart 1, which is at atmospheric pressure, exits from the analysis chart 1 via the tube 5 through the inoculum 3 and makes room for the inoculum 3 which thus goes back up the tube 5 into the analysis chart 1. Conversely, it is possible to apply a pressure of air on the inoculum via the open end of the tube 4 in order to cause the inoculum 3 to go back up the tube 5. The biological sample formed by the inoculum is then in place in an analysis receptacle 2.

The analysis instrument comprises a holographic imaging system with a field of view configured for acquiring a holographic image of this field of view. The acquisition of a holographic image allows a large depth of field, and hence a very good sensitivity for detection of biological agents. For the acquisition of a holographic image, the holographic imaging system is placed opposite an analysis receptacle 2. By way of non-limiting example, FIG. 2 shows schematically an in-line holographic imaging system 10 disposed such that the field of view 11 of said holographic imaging system 10 is contained within the volume of biological sample contained in an analysis receptacle 2. The analysis chart 1, and hence the analysis receptacles 2 that it comprises, is placed in an object plane of the holographic imaging system 10. The holographic imaging system 10 defines an imaging axis 16, here simplified by a line corresponding to the optical axis but which may consist of a set of successive lines defining the light path, depending on the configuration of the optical components of the holographic imaging system 10.

On one side of the analysis receptacle 2, here on the optical axis 16, a light source 4 is located configured for illuminating the analysis receptacle 2 in the field of view of the holographic imaging system 10 by means of an illuminating beam of sufficiently coherent light. The light source 14 may produce the illuminating light, or be simply the termination of an optical fiber carrying this illuminating light, potentially fitted with an iris. The illuminating beam exhibits the conventional characteristics for holographic imaging, without any particular additional limitations. The illuminating beam may thus be monochromatic (for example with a wavelength of around 640-670 nm) or may possibly be composed of several wavelengths, for example used one after the other.

On the other side of the analysis receptacle 2, here on the optical axis 16, an image sensor 12 is located, which is a digital sensor such as for example a CMOS or CCD sensor. The image sensor 12 is placed on an image plane of the holographic imaging system 10 and is configured for acquiring a hologram, in other words a spatial distribution of intensity of the interferences caused by interactions between the inoculum placed in the field of view 11 and the illuminating beam.

The holographic imaging system 10 here is equipped with an assembly of optical elements 18 disposed between the analysis receptacle 2 and the digital image sensor 12 such as for example a microscope objective lens 18a and a tube lens 18b in the example illustrated. An optical element such as the microscope objective lens 18a is however optional, the invention not being limited to the holographic microscopy with lens. The arrangement described here is of course one non-limiting example. Any holographic imaging system 10 may be used, with various optical elements (with or without microscope objective lens, etc.). Thus, as long as a holographic imaging system 10 can acquire an image in which the interference patterns generated by the biological sample appear, this holographic imaging system is suitable for the implementation of the method. Preferably, however, the holographic imaging system 10 is configured for defining a depth of field of at least 100 µm of depth in the direction of the optical axis 16 around each acquisition focal plane 20, and preferably at least 150 µm, and more preferably at least 250 µm. Typically, the analysis receptacle 2 comprises two opposing transparent faces 2a, 2b arranged along the optical axis 16, and the depth of field extends over at least 100 µm between the two opposing transparent faces of the analysis receptacle, and preferably over at least 150 µm, and more preferably over at least 250 µm, or even at least 300 µm. The field of view 11 extends as being the space in which the presence of biological agents may be determined from a hologram imaging said field of view 11.

The measurement instrument also comprises components allowing data to be processed, such as a processor, a memory, communications buses, etc. Given that these other components are only specific by the method that they implement and by the instructions that they contain, they will not be detailed in the following.

FIG. 3 is a diagram illustrating steps of the analysis method, which follow the initial installation (step S1) of the biological sample in an analysis receptacle 2 in the field of view 11 of a holographic imaging system 10, detailed hereinabove. The method comprises a plurality of cycles (steps S02) composed of steps implemented in a repeated fashion for a plurality of measurement times of a measurement period:

the acquisition of a plurality of holographic images of the biological sample at various respective positions on the optical axis 16 of the acquisition focal plane, the determination, from each acquired holographic image, of a value of a biomass parameter representative of the quantity of biological agents at said position of the acquisition focal plane.

These cycles are typically repeated according to a period going from one minute to 30 minutes, depending on the speed of the analysis instrument, on the number of biological samples processed in parallel, and for example depending on the number of analysis receptacles 2 in an analysis chart 1.

The measurement period extends over several hours, and typically more than 10 hours, resulting in several tens or even several hundreds of measurement times.

It goes without saying that the acquisition of a plurality of holographic images of the biological sample at various respective positions on the optical axis 16 of the acquisition focal plane implies a movement of the acquisition focal plane (step S02c) prior to each acquisition of a holographic image by the image sensor 12 (step S02a). These various positions of the acquisition focal plane may be obtained for example by moving the whole assembly formed by the image sensor 12 and the optical elements 18a, 18b, for example via a motorized rail or a motorized turntable. It is also possible to obtain these various positions of the acquisition focal plane 20 by the modification of an optical element of the holographic imaging system 10 moving the acquisition focal plane, by modifying the focusing of light radiation incident on the image sensor 12 in such a manner as to displace the acquisition focal plane of the image sensor 12.

The various respective positions on the optical axis 16 of the acquisition focal planes number at least 2 in the analysis receptacle, preferably at least 5, and more preferably at least 15, although only six of them are illustrated in FIG. 4 for the sake of simplicity. A greater number of acquisition planes allows the analysis of the non-uniformity of the spatial distribution of the biological agents along the optical axis 16 to be refined. It should be noted that the acquisition focal planes preferably extend in a substantially perpendicular manner to the optical axis 16, such that the various respective positions on the optical axis 16 correspond to as many different depths within the analysis receptacle 2.

As previously mentioned, the analysis receptacle 2 typically comprises two opposing transparent faces 2a, 2b situated at various positions on the optical axis 16, and various respective positions 20a, 20b, 20c, 20d, 20e, 20f on the optical axis 16 of the acquisition focal planes 20 extend from one transparent face 2a, 2b to the other transparent face 2a, 2b. Preferably, various respective positions 20a, 20b, 20c, 20d, 20e, 20f are regularly spaced out along the optical axis 16 between the two opposing transparent faces 2a, 2b. Preferably, the various respective positions 20a, 20b, 20c, 20d, 20e, 20f of the acquisition focal plane are spaced out in such a manner that each image acquired makes different biological agents appear. Typically, the various respective positions 20a, 20b, 20c, 20d, 20e, 20f of the acquisition focal plane on the optical axis 16 extend over a depth, along the optical axis 16, of greater than 0.1 mm, and preferably greater than or equal to 0.5 mm, and preferably greater than or equal to 0.8 mm. Preferably, consecutive positions 20a, 20b, 20c, 20d, 20e, 20f of the acquisition focal plane on the optical axis 16 are spaced out by at least 50 μm, preferably by at least 100 μm, and more preferably by at least 150 μm.

The regions close to the two transparent faces 2a, 2b constitute favored regions for analysis of the spatial distribution of the biological agents. Aside from the fact that the reagents may be present on at least one of these transparent faces 2a, 2b, these faces also form mechanical substrates on which the biological agents can develop a biofilm, a particularly interesting feature to be detected. In order to ensure that a region in immediate proximity to one of the two transparent faces 2a, 2b is correctly imaged, it is possible to arrange for at least one position of an acquisition focal plane on the optical axis 16 not to be situated between the two transparent faces 2a, 2b and, more precisely, that at least two positions of acquisition focal planes on the optical axis 16 are on either side of other of a transparent face 2a, 2b.

Ideally, one position of an acquisition focal plane on the optical axis 16 corresponds to the position of a transparent face 2a, 2b.

During the acquisition of a holographic image, the holographic imager 10 acquires a hologram, which offers the advantage of a large depth of field, and hence a high sensitivity for detection of the biological agents in the biological sample. During the acquisition of a holographic image, the holographic imaging system acquires a hologram. During the acquisition of a hologram, the light source 14 emits a reference illuminating beam, which may correspond to a reference plane wave propagating in the direction Z along the imaging axis 16. The biological agents present in the field of view 11 inside the analysis receptacle 2, by their diffraction properties, scatter the incident reference light. The wave scattered by the biological agents and the reference wave interfere on the image sensor 12 so as to form the hologram. Since a digital image sensor 12 is only sensitive to the intensity of the electromagnetic field, the hologram corresponds to the spatial intensity distribution of the total field corresponding to the addition of the scattered wave and of the reference wave, which corresponds to a value of gray level for each pixel. The holographic image used may be the hologram or may be an image reconstructed by a back-propagation calculation based on the hologram, using a propagation algorithm for example based on the Rayleigh-Sommerfeld diffraction theory. Using the hologram without reconstruction allows a high detection sensitivity to be obtained, since each biological agent appears in the hologram surrounded by rings corresponding to the interference figures caused by the presence of said biological agents, facilitating accordingly the detection of the presence of these biological agents. Furthermore, the non-reconstruction allows a gain in time and in processing resources. However, using a reconstructed image offers other advantages, such as that of allowing the biological agents appearing in the reconstructed image to be precisely localized, potentially in three dimensions. As for the hologram, such a reconstructed image may be defined by gray levels for each pixel.

Preferably, the biomass parameter of a holographic image is derived from a statistic relating to the gray levels of the pixels of said holographic image, and more preferably, the biomass parameter is an average of the absolute values of the gray levels of each pixel of the holographic image. Other biomass parameters may however be used, such as for example a counting of the biological agents appearing in the holographic image, or else the proportion of the holographic image in which biological agents appear or do not appear.

Preferably, the determination of the biomass parameter of a holographic image comprises a prior normalization of the holographic image, comprising:

the determination of a background image by application of a smoothing filter, preferably a Gaussian filter, to the acquired holographic image, the division pixel to pixel of the gray levels of the acquired holographic image by the gray levels of the background image.

The parameters of the smoothing filter, for example the standard deviation for a Gaussian filter, are chosen so as to create a low-pass filter with a cut-off frequency that is low enough for the filtered image to only be representative of the background of the holographic image, hence the name background image, without for example the biological agents being discernable in this filtered image. The normalization of the image may furthermore comprise a subtraction of a constant applied to the gray levels of the holographic image resulting from the division. A normalized holographic image may then be obtained with negative values of gray levels. It is therefore the absolute values of the gray levels that are taken into account for determining the values of the biomass parameter.

Following a measurement cycle, which allows a plurality of values of the biomass parameter to be obtained at the same measurement time for various positions of the acquisition focal plane, a distribution indicator is constructed (step S03) based on values of the biomass parameter from the same measurement time for several positions of the acquisition focal plane. The distribution indicator is representative of the spatial distribution of the quantity of biological agents along the optical axis at this measurement time. For example, the distribution indicator may be obtained by spatially organizing the biomass parameters according to the respective positions of their acquisition focal planes. Typically, the distribution indicator takes the form of a concatenation of the values of the biomass parameter, and preferably takes the form of a spatial concatenation, in which the values of the biomass parameter are spatially concatenated. The distribution indicator may therefore be interpreted as a vector whose components correspond to the quantity of biological agents at various positions. Typically, the various values of the biomass parameter are organized according to the same spatial organization as the respective positions of the acquisition focal planes of the holographic images from which they come. It is also possible for the distribution indicator to correspond to a single value, which corresponds to the uniformity or to the non-uniformity of the spatial distribution of the quantity of biological agents along the optical axis at one measurement time. The distribution indicator may thus be obtained by a calculation applied to values of biomass parameters at various acquisition focal planes and, in particular, by differences between these values. For example, a distribution indicator may correspond to a difference between at least one value of the biomass parameter with an acquisition focal plane close to the middle of the well (on the optical axis), and at least one value of the biomass parameter with an acquisition focal plane close to a transparent face 2a, 2b. Other calculations are possible, such as for example a standard deviation, a variance, or other.

Thus, again taking the example in FIG. 4, a first holographic image is acquired with an acquisition focal plane 20 at a first position 20a, then a second holographic image is acquired with an acquisition focal plane 20 at a second position 20b, then a third holographic image is acquired with an acquisition focal plane 20 at a third position 20c, etc., until a holographic image has been acquired for each position 20a, 20b, 20c, 20d, 20e, 20f of the acquisition focal plane 20 along the optical axis. A value of the biomass parameter is determined for each holographic image, and hence is associated with each position 20a, 20b, 20d, 20e, 20f: a first value for the first position 20a, a second value for the second position 20b, a third value for the third position 20c, etc. In order to construct the distribution indicator, the first value is therefore placed adjacent to the second value, itself placed adjacent to the third value, itself placed adjacent to the fourth value, etc. The second value is therefore between the first value and the third value, just as the second position 20b is between the first position 20a and the third position 20c. The spatial organization of the respective positions of the acquisition focal planes is therefore recovered.

Each measurement cycle therefore allows a distribution indicator to be obtained that is representative of the spatial distribution of the quantity of biological agents along the optical axis 16 at the measurement time during which the cycle occurs. The measurement cycles are typically repeated with a period going from one minute to 30 minutes, depending on the speed of the analysis instrument, on the number of biological samples processed in parallel, and for example depending on the number of analysis receptacles 2 in an analysis chart 1, but also as a function of the speed of the interactions between the biological agents and the reagents. The duration of analysis typically extends over several hours, and the method thus comprises typically more than 10 cycles, and preferably more than 20 measurement cycles during this measurement period.

Following these measurement cycles, corresponding to a plurality of measurement times, a plurality of distribution indicators is therefore obtained representative of the spatial distribution of the quantity of biological agents along the optical axis 16 at a plurality of measurement times. Preferably, the method subsequently comprises the construction (S04) of a representation of the distribution of the biomass of biological agents, which is derived from at least one distribution indicator at one measurement time. Preferably, the representation of the distribution of the biomass of biological agents is a representation of the time variation of the distribution of the biomass of biological agents which is derived from several distribution indicators at a plurality of measurement times. This representation of the distribution of the biomass of biological agents may be constructed by spatially organizing distribution indicators according to their respective measurement times. This is because each distribution indicator corresponds to a particular measurement time. The combination of the distribution indicators therefore allows the time variation of the spatial distribution of the biomass of biological agents along the optical axis 16 to be monitored. Preferably, this is a concatenation of distribution indicators, organized chronologically.

Figure 5:
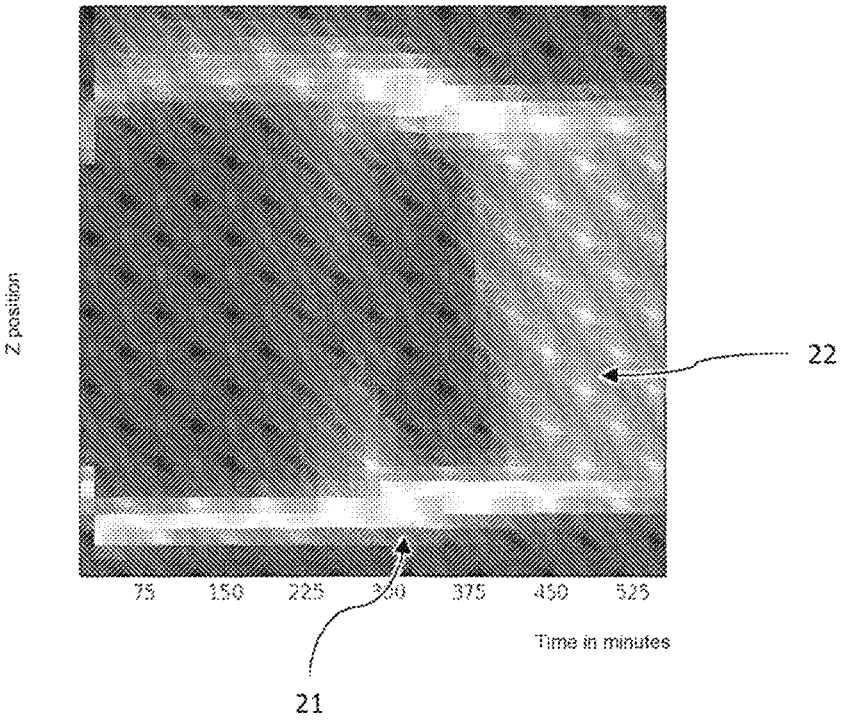
FIG. 5 is one example of a graphical representation of the variation over time of the spatial distribution of biomass of biological agents along an optical axis.

FIG. 5 shows one example of a representation of this time variation. The biological sample imaged is a suspension in a saline solution of *Pseudomonas aeruginosa* as biological agents. At each measurement time, 27 holographic images have been acquired at 27 acquisition position focal planes along the optical axis, which corresponds to 27 different depths. The measurement times are spaced out by 15 minutes. Thus, in FIG. 5, the ordinate axis is that of the Z positions along the optical axis, corresponding to the depth, and the abscissa axis is that of time, in minutes. The bottom of the figure therefore corresponds to a transparent face 2a, 2b of the analysis receptacle 2, and the top of the figure corresponds to the other transparent face 2a, 2b, whereas the left of the figure corresponds to the start of the measurement period and the right of the figure corresponds to the end of the measurement period.

This figure corresponds to a representation of the distribution of the biomass of biological agents in graphical form, derived from the distribution indicators at several measurement times, which has been obtained by translating the values of the biomass parameter into various gray levels. An increase of the biomass of bacteria with time (from left to right) is observed, but also that the distribution in depth of the biomass is not uniform and varies with time: the growth of the bacteria firstly occurs in a region 21 close to a face, then diffuses into the center 22 of the analysis receptacle 2. In fact, the bacteria *Pseudomonas aeruginosa* develop in the form of structured clusters called biofilms, which firstly extend over the surfaces of the analysis receptacle 2. Thus, the spatial distribution of the biological agents within the analysis receptacle is important information, which may for example constitute an additional indicator for identifying the biological agents of the sample, or for evaluating the interactions with reagents disposed on one face of the analysis receptacle 2, or else for revealing the capacity of the biological agent to form a biofilm.

Consequently, the method comprises the supply, from amongst the analysis results (step S05), of the representation of the distribution of the biomass of biological agents derived from at least one distribution indicator at one measurement time, for example to provide information on the spatial distribution of the biological agents at one measurement time. This representation of the distribution of the biomass of biological agents may for example be supplied in graphical form, such as an image or a curve or a table. It may be supplied in the form of numerical values, for example corresponding to one or more distribution indicators. It is furthermore possible for the representation of the distribution of the biomass of biological agents to simply be one of the distribution indicators, in which case no construction step may be necessary, except for example if it is desired to supply this representation of the distribution of the biomass of biological agents graphically. Thus, even with only one distribution indicator composed of values of the biomass parameter, it is possible to construct a curve showing the distribution of the biomass of biological agents along the optical axis.

A representation of the time variation of the distribution of the biomass of biological agents may for example be obtained by spatially organizing distribution indicators according to their respective measurement times. The image in FIG. 5 is one example of such a representation in graphical form. However, this representation of the distribution of the biomass of biological agents may take another form, such as for example a curve or a table or even a numerical value, as previously mentioned. By way of example, when the distribution indicators are numerical values, the representation may be a table or a list organizing chronologically said numerical values of the distribution indicators, or representing it in the form of curves. The representation of the distribution of the biomass of biological agents may also result from a calculation relating to values of distribution indicators, such as for example differences between these values.

The representation of the distribution of the biomass of biological agents here is understood as allowing its communication to an operator and its interpretation by the latter. The representation of the distribution of the biomass of biological agents may for example be displayed on a display screen, in a format allowing its display, or may be transmitted to a printer in order to be printed.

The invention is not limited to the embodiment described and shown in the appended figures. Modifications remain possible, notably from the point of view of the composition of the various technical features or by substitution of equivalent techniques, without however straying from the field of protection of the invention.

The invention claimed is:

1. A method for analyzing a biological sample by means of an analysis instrument, the biological sample comprising biological agents and being disposed in an analysis receptacle in a field of view of a holographic imaging system, the holographic imaging system defining an optical axis and an acquisition focal plane, the method comprising, for each measurement time from a plurality of measurement times of a measurement period:

the acquisition of a plurality of holographic images of the biological sample at various respective positions on the optical axis of the acquisition focal plane, the determination, from each acquired holographic image, of a value of a biomass parameter representative of the quantity of biological agents at the position of the acquisition focal plane of said holographic image, the method comprising the construction of a distribution indicator using values of the biomass parameter from the same measurement time for several positions of the acquisition focal plane, the distribution indicator being representative of the spatial distribution of the quantity of biological agents in the analysis receptacle along the optical axis at a measurement time, and the provision, from amongst the analysis results, of a representation of the distribution of the biomass of biological agents derived from at least one distribution indicator at one measurement time.

2. The method as claimed in claim 1, in which the distribution indicator is obtained by spatially organizing values of the biomass parameters according to the respective positions of the acquisition focal plane or the distribution indicator is obtained by a calculation applied to values of biomass parameters at various positions of the acquisition focal plane.

3. The analysis method as claimed in claim 1, in which the representation of the distribution of the biomass of biological agents is a representation of the time variation of the distribution of the biomass of biological agents which is derived from several distribution indicators at a plurality of measurement times.

4. The analysis method as claimed in claim 3, comprising the construction of the representation of the time variation of the distribution of the biomass of biological agents by spatially organizing distribution indicators according to their respective measurement times.

5. The analysis method as claimed in claim 1, in which the biomass parameter of a holographic image is derived from a statistic relating to the gray levels of the pixels of said holographic image and/or the biomass parameter is an average of the absolute values of the gray levels of each pixel of the holographic image.

6. The analysis method as claimed in claim 1, in which the determination of the biomass parameter of a holographic image comprises a prior normalization of the holographic image, comprising:

the determination of a background image by application of a smoothing filter to the acquired holographic image, the division pixel to pixel of the gray levels of the acquired holographic image by the gray levels of the background image.

7. The analysis method as claimed in claim 1, in which the various respective positions on the optical axis of the acquisition focal planes number at least 10 in the analysis receptacle.

8. The analysis method as claimed in claim 1, in which the analysis receptacle comprises two opposing transparent faces situated at various positions on the optical axis, and the various respective positions on the optical axis of the acquisition focal planes extend from one transparent face to the other transparent face.

9. The analysis method as claimed in claim 8, in which at least one position of an acquisition focal plane on the optical axis is not situated between the two transparent faces, and/or a position of an acquisition focal plane on the optical axis corresponds to the position of a transparent face.

10. The analysis method as claimed in claim 1, in which the holographic imaging system defines a depth of field of at least 100 μm of depth in the direction of the optical axis around each acquisition focal plane.

11. The analysis method as claimed in claim 1, in which the plurality of holographic images are holograms or images reconstructed from holograms.

12. An analysis instrument comprising a holographic system with a field of view configured for acquiring a holographic image and data processing means, the analysis instrument being configured for receiving a biological sample in an analysis receptacle in the field of view of the holographic system and for implementing the steps of the method as claimed in claim 1.

* * * * *